United States Patent [19]

Harris

[11] 4,313,013

[45] Jan. 26, 1982

[54] PALLADIUM OR A PALLADIUM ALLOY HYDROGEN DIFFUSION MEMBRANE TREATED WITH A VOLATILE COMPOUND OF SILICON IS USED TO SEPARATE HYDROGEN FROM A MIXTURE OF IT WITH A HYDROCARBON

[75] Inventor: Jesse R. Harris, Bartlesville, Okla.

[73] Assignee: Phillips Petroleum Company, Bartlesville, Okla.

[21] Appl. No.: 174,468

[22] Filed: Aug. 1, 1980

[51] Int. Cl.$^3$ .............................................. C07C 7/144
[52] U.S. Cl. .................................. 585/818; 585/660; 585/661; 585/654; 585/440; 585/441; 585/443
[58] Field of Search ......................................... 585/818

[56] References Cited

U.S. PATENT DOCUMENTS

| | | | |
|---|---|---|---|
| 3,450,500 | 6/1969 | Setzer et al. | 585/818 X |
| 3,758,605 | 9/1973 | Hughes et al. | 585/818 |
| 3,770,842 | 11/1973 | Steigelmann et al. | 585/818 X |
| 3,784,624 | 1/1974 | Perry et al. | 585/818 |
| 3,865,890 | 2/1975 | Steigelmann et al. | 585/818 X |

*Primary Examiner*—Paul F. Shaver

[57] ABSTRACT

A palladium or palladium alloy hydrogen diffusion membrane which has been treated with silane and/or silicon tetrafluoride is employed to separate hydrogen from a hydrocarbon with which it is in admixture and from which it may have been produced under dehydrogenation conditions in the presence of said membrane.

7 Claims, No Drawings

PALLADIUM OR A PALLADIUM ALLOY HYDROGEN DIFFUSION MEMBRANE TREATED WITH A VOLATILE COMPOUND OF SILICON IS USED TO SEPARATE HYDROGEN FROM A MIXTURE OF IT WITH A HYDROCARBON

BRIEF DESCRIPTION OF THE INVENTION

A palladium or palladium alloy hydrogen diffusion membrane is treated with a volatile compound of silicon, silane, and/or silicon tetrafluoride. The volatile compound chosen is one which is effective at some temperature to deposit a protective layer of silicon on the diffusion membrane and to increase its resistance to poisoning by deposition of the carbonaceous materials.

DETAILED DESCRIPTION

This invention relates to the recovery of hydrogen from a mixture of it with a hydrocarbon. It also relates to the treatment of a hydrocarbon with a palladium dehydrogenation catalyst to produce hydrogen and to the recovery of hydrogen produced by diffusion through the palladium. In one of its aspects, the invention relates to the use of a pretreated palladium or palladium alloy hydrogen diffusion membrane or material.

In one of its concepts, the invention provides a process for the separation of hydrogen from a mixture of it with a hydrocarbon which comprises subjecting the mixture to contact with a hydrogen diffusion membrane consisting essentially of palladium or a palladium alloy which has been treated with at least one volatile compound of silicon effective at a temperature of treatment to produce on the palladium diffusion membrane a very thin layer of silicon effective to extend the time of use of the membrane prior to having to regenerate the same due to poisoning by deposition thereon of a carbonaceous deposit. In a more specific concept of the invention, the treating agent or deposition of the silicon to form a film that may be no more than one or more monomolecular layers, is at least one compound selected from silane ($SiH_4$) and silicon tetrafluoride ($SiF_4$).

It is an object of this invention to recover hydrogen. It is another object of this invention to produce hydrogen. It is a further object of this invention to separate hydrogen from mixtures containing it and a hydrocarbon.

Other aspects, concepts, objects and the several advantages of the invention are apparent from a study of this disclosure and the appended claims.

According to the present invention, there is provided a process for the recovery of hydrogen, as in a hydrocarbon dehydrogenation process, by subjecting a flow of a mixture of hydrocarbon and hydrogen to contact with a palladium or palladium alloy hydrogen diffusion or contact mass which has been treated with a volatile compound of silicon under conditions effective to deposit a layer of silicon on the diffusion membrane a selected compound being effective to yield such a layer which will prolong the period of time between regeneration which otherwise is required apparently due to deposition of carbonaceous materials.

One skilled in the art in possession of this disclosure can determine by test the silicon containing compounds effective to yield the optimum results sought.

It will be noted that silane and silicon tetrafluoride decompose under the conditions of treatment and that the products of decomposition are such as not to adversely affect the palladium or the palladium alloy. Presently, silicon tetrafluoride is preferred at least because it is convenient to use.

It is known that palladium and certain alloys that comprise palladium are selectively permeable to hydrogen. A consequence of this property is that the equilibrium of gas phase reactions in which hydrogen is reactant or a product can be affected by the presence of such a hydrogen permeable membrane. The process of dehydrogenation of hydrocarbons, e.g., the conversion of paraffins to monoolefins plus hydrogen—$C_nH_{2n+2} \rightleftharpoons C_nH_{2n} + H_2$—is exemplary of such reactions. The use of palladium membranes to affect favorably the conversion and selectivity of such reactions has already been studied. U.S. Pat. No. 3,290,406 discloses and claims such a process. The disclosure of the patent is incorporated by this reference.

Ordinarily, the temperatures at which hydrocarbon dehydrogenation is to be effected are such as to cause the palladium membrane to become poisoned, thus inhibiting the passing of hydrogen through the membrane, destroying its effectiveness for the separation of hydrogen. As noted, regeneration is frequently required due to deposition of carbonaceous material on the membrane.

Hydrogen permeable membranes to which this process is applicable comprise palladium and its alloys with metals from Groups IB, IIIB, and VIII of the periodic table of the elements that contain not less than 50 weight percent of palladium. Suitable alloying metals are silver, yttrium, and nickel.

Membranes are treated after they have been fabricated into the shape in which they will be used. Prior to treatment, it is essential that the membranes be carefully cleaned. After washing with a suitable solvent, if necessary, the membrane is subjected to oxidations with a free oxygen-containing gas at a suitable temperature for removal of carbonaceous residue. The temperature can range from about 200° C. up to the melting (or deformation) temperature of the membrane, and the time of oxidation generally is inversely related to the temperature, from about a minute to an hour. The membrane is then reduced in an atmosphere comprising hydrogen, preferably relatively pure hydrogen, for at least 5 but preferably about 30 minutes at 300°–400° C. Both the oxidation and the reduction are done, for convenience, at about atmospheric pressure although sub- or superatmospheric pressures can be used. Static or flowing gas for both operations can be used; generally flowing gas is preferred to remove reaction products from the membrane.

After pretreatment as described the membrane is treated on the side that will be contacted with organic compounds with the chosen compound of silicon at conditions sufficiently severe to decompose said compound and deposit a film of elemental silicon. The volatile silicon compound can be used alone, or diluted with a suitable inert gas such as hydrogen, helium, nitrogen, or argon. Either static or flowing gas can be used. The partial pressure of the silicon compound preferably is at least one kPa. Total pressure for the treating gas preferably will be about 100 kPa (atmospheric) for convenience, but higher pressures can be used. Temperatures for treatment are between about 350°–450° C. at contact times of 0.1 to 10 hours; time of about one hour is generally preferred.

The following examples illustrate the invention.

EXAMPLE I

A 75 wt. % palladium—25 wt. % silver membrane was used in runs to separate hydrogen from hydrogen-ethylene mixture. To a tubular specimen that was 13.0 cm. (5.125 in.) long×0.1588 cm. (0.0625 in.) o.d.×0.0102 cm. (0.004 in.) wall thickness extensions of 0.318 cm. (0.125 in.) o.d. stainless steel tubing were attached by gold brazing. The membrane was secured concentrically in a 0.953 cm. (0.375 in.) o.d. stainless steel tube having 0.0762 cm. (0.030 in.) wall thickness with Swagelok connectors and provision was made for two separate gas streams to pass through the membrane and through the outer annulus. Before starting the run the membrane was prepared by heating in flowing air for 15 min. at 350° C., purged with argon, reduced with flowing hydrogen for 30 min. at 350° C. and again purged with argon. In this treatment the gases contacted both sides of the membrane. After the run, made as described below, the membrane was again treated as outlined above but, after the second purge with argon was contacted on the inside only with 134 kPa of $SiF_4$ for an hour at 450° C. $SiF_4$ was purged from the membrane with argon and it was again used in a run.

Runs with the untreated, then treated membrane were made in the same way, as follows. Hydrogen gas with or without added ethylene (both were metered with flowmeters) flowed through the membrane tube at superatmospheric pressure. The rate at which gas left the tubular membrane was measured with a soap film buret. This rate generally was lower than the feed rate because of loss of hydrogen by diffusion through the wall of the membrane. (Hydrogen was also consumed at times by hydrogenating the ethylene to ethane; this was determined by GLC analysis of effluent gas). Argon flowed at a measured rate through the annulus to sweep away hydrogen that had diffused through the membrane. The argon stream was also analyzed by GLC to determine its hydrogen content and its flow rate was also measured with soap film buret. Table I summarizes the run made with the untreated 75 Pd-25 Ag membrane in Part A; Part B summarizes the run with the same membrane after silicon treatment. The membrane was maintained at 450° C. throughout both runs.

The experimental rate at which hydrogen permeated the membrane at the start of each run is used to calculate the flux ($H_2$flux calc.) in the absence of poisoning for each experimental value of $P_F^{\frac{1}{2}} - P_p^{\frac{1}{2}}$. The actual measured fluxes are then compared with these calculated fluxes using the ratio meas/calc. A ratio of 1.00 indicates no poisoning while values less than 1.00 indicate poisoning. Values greater than 1.00 may result from errors in approximating the hydrogen partial pressure along the membrane and from instabilities in the surface composition of the membrane. Part A of Table I shows that after 90 minutes of exposure to ethylene the permeability of the untreated membrane was essentially destroyed (Ratio=0). In contrast, Part B of that Table shows that the membrane retained a substantial fraction (Ratio=0.59) of its permeability after 120 minutes of exposure to ethylene.

TABLE I

| Sample | Time, min. | Total pres., kPa Feed[a] | Total pres., kPa Product[b] | $H_2$ pres., kPa Feed | $H_2$ pres., kPa Product | $P_F^{\frac{1}{2}} - P_p^{\frac{1}{2}c}$ | $H_2$ flux (meas.) mL/min. | $H_2$ flux[d] (calc.) mL/min. | Ratio: Meas/Calc. |
|---|---|---|---|---|---|---|---|---|---|
| Part A - Untreated Membrane ||||||||||
| 1 | 30 | 168 | 119 | 168 | 25 | 8.0 | 54 | 54 | 1.00 |
| 2 | 60 | 169 | 118 | 121 | 19 | 6.6 | 38 | 45 | .84 |
| 3 | 90 | 169 | 118 | 124 | 18 | 6.9 | 36 | 47 | .77 |
| 4 | 120 | 170 | 116 | 88 | 0 | 9.4 | 0 | 63 | .00 |
| 5 | 150 | 170 | 115 | 90 | 0.7 | 8.7 | 1 | 59 | .02 |
| 6 | 165 | 169 | 115 | 169 | 0 | 13.0 | 0 | 88 | .00 |
| 7 | 180 | 169 | 115 | 169 | 0 | 13.0 | 0 | 88 | .00 |
| Part B - Silicon-treated Membrane ||||||||||
| 8 | 30 | 167 | 126 | 167 | 24 | 8.0 | 46 | 46 | 1.00 |
| 9 | 60 | 167 | 125 | 130 | 19 | 7.0 | 33 | 40 | .83 |
| 10 | 90 | 167 | 125 | 130 | 19 | 7.0 | 33 | 40 | .83 |
| 11 | 120 | 168 | 123 | 75 | 11 | 5.6 | 19 | 32 | .59 |
| 12 | 150 | 168 | 123 | 75 | 11 | 5.6 | 19 | 32 | .59 |
| 13 | 165 | 167 | 125 | 167 | 21 | 8.3 | 38 | 48 | .79 |
| 14 | 180 | 168 | 125 | 168 | 21 | 8.3 | 37 | 48 | .77 |

[a]$H_2$ only in samples 1, 6, 7, 8, 13, 14; $H_2$ + $C_2H_4$ in remaining samples.
[b]Argon + $H_2$ diffused through membrane.
[c]Calculated from the partial pressure of $H_2$ in the feed and product. Fick's Law and Sievert's Law state that:

$$H_2 Flux = \frac{DKA}{x} (P_1^{\frac{1}{2}} - P_2^{\frac{1}{2}})$$ where D = Fick's diffusion coefficient, K = Proportionality constant including the equilibrium constant for hydrogen dissociation, $P_1$ and $P_2$ are high and low $H_2$ partial pressures. A = membrane area, x = membrane thickness. For identical membranes this reduces to $H_2 Flux = k(P_1^{\frac{1}{2}} - P_2^{\frac{1}{2}})$

[d]$H_2$ flux (measured) = $H_2$ flux (calculated) for samples 1 and 8. Other values calculated using k in note c above.

EXAMPLE II

A 95 wt. % palladium—5 wt. % nickel membrane was used in runs to separate hydrogen from hydrogen-ethylene mixture. A tubular specimen that was 14.2 cm. (5.6 in.) long but having dimensions otherwise identical with the Pd-Ag membrane described in Example I was mounted in an identical manner. Before the run was made the sample was treated with air, then hydrogen, just as described in the preceding example. After that run was completed the membrane was treated with $SiF_4$ as described above and the run again was repeated. Table II summarizes the run made with the untreated 95Pd-5Ni membrane in Part A; Part B summarizes the run with the same membrane after silicon treatment. Again the membrane was maintained at 450° C. throughout both runs.

Results from both runs, which were made in an identical manner, suggest that the treatment with silicon may have reduced slightly the permeability of the Pd-Ni membrane (compare samples 1 and 8). However, in all samples taken when ethylene was present in the feed, viz, samples at 60, 90, 120, and 150 minutes, the measured to calculated ratio of hydrogen flux through the membrane was greater for the silicon-treated membrane than for the untreated membrane. This demonstrates that the treated membrane was more permeable to hydrogen in the presence of ethylene.

TABLE II

| Sample | Time, min. | Total pres. kPa Feed | Total pres. kPa Product | H₂ pres., kPa Feed | H₂ pres., kPa Product | flux $P_F^{\frac{1}{2}} - P_P^{\frac{1}{2}}$ | H₂ flux (Meas) mL/min | H₂ Ratio: (Calc) mL/min | Meas/ Calc |
|---|---|---|---|---|---|---|---|---|---|
| Part A - Untreated Membrane ||||||||||
| 1 | 30 | 168 | 105 | 168 | 30 | 7.5 | 20 | 20 | 1.00 |
| 2 | 60 | 170 | 105 | 67 | 19 | 3.8 | 11 | 10 | 1.10 |
| 3 | 90 | 170 | 105 | 69 | 17 | 4.2 | 10 | 11 | 0.91 |
| 4 | 120 | 170 | 105 | 71 | 14 | 4.7 | 8 | 13 | 0.62 |
| 5 | 150 | 170 | 105 | 71 | 14 | 4.7 | 8 | 13 | 0.62 |
| 6 | 165 | 169 | 103 | 168 | 25 | 8.0 | 16 | 21 | 0.76 |
| 7 | 180 | 168 | 105 | 168 | 27 | 7.8 | 17 | 21 | 0.81 |
| Part B - Silicon-Treated Membrane ||||||||||
| 8 | 30 | 169 | 108 | 169 | 30 | 7.5 | 19 | 19 | 1.00 |
| 9 | 60 | 169 | 106 | 72 | 21 | 3.9 | 12 | 10 | 1.20 |
| 10 | 90 | 170 | 108 | 74 | 19 | 4.2 | 11 | 11 | 1.00 |
| 11 | 120 | 170 | 108 | 76 | 17 | 4.6 | 10 | 12 | 0.83 |
| 12 | 150 | 170 | 108 | 77 | 18 | 4.5 | 10 | 11 | 0.91 |
| 13 | 165 | 171 | 108 | 171 | 25 | 8.1 | 15 | 21 | 0.71 |
| 14 | 180 | 170 | 109 | 170 | 27 | 7.8 | 16 | 20 | 0.80 |

Reasonable variation and modification are possible within the scope of the foregoing disclosure and the appended claims to the invention, the essence of which is that a hydrogen diffusion membrane consisting essentially of palladium has been rendered resistant to poisoning as when used for the separation of hydrogen, as producing hydrogen, in the conversion or dehydrogenation of a hydrocarbon by treating the membrane with a compound of silicon effective to coat or to lay down on the membrane a thin layer of silicon, as described.

I claim:

1. A process for the separation of hydrogen from a mixture of it and a hydrocarbon in the presence of a palladium hydrogen diffusion membrane which comprises pretreating said membrane with a compound of silicon at an elevated temperature effective to lay down on the membrane a thin layer of silicon and then subjecting hydrocarbon to said conditions under which hydrogen is separated therefrom.

2. A process according to claim 1 wherein the membrane is treated with at least one of silane and silicon tetrafluoride.

3. A process according to claim 1 wherein the hydrogen is in admixture with at least ethylene.

4. A process according to claim 1 wherein the treatment of the membrane is effected at a temperature in the approximate range of from about 250°–450° C. and at a contact time in the approximate range of from 0.1 to 10 hours.

5. A process according to claim 1 wherein the membrane after thorough cleaning by oxidation and subsequent reduction is contacted for about 1 hour at a temperature of about 450° C. with silicon tetrafluoride.

6. A process according to claim 5 wherein the membrane is contacted on one side with silicon tetrafluoride at a pressure just slightly above atmospheric.

7. A process according to claim 1 wherein the mixture is produced by a dehydrogenation operation.

* * * * *